(12) United States Patent
Hampton, Jr. et al.

(10) Patent No.: US 8,710,278 B1
(45) Date of Patent: Apr. 29, 2014

(54) PROCESS FOR PRODUCING POLYOLS

(71) Applicant: Eastman Chemical Company, Kingsport, TN (US)

(72) Inventors: Kenneth Wayne Hampton, Jr., Gilmer, TX (US); Eugene H. Brown, Gilmer, TX (US); Thomas K. Brown, Hallsville, TX (US); Amy K. Paris, Kingsport, TN (US); Kevin S. Howe, Longview, TX (US); Thomas Allen Puckette, Longview, TX (US)

(73) Assignee: Eastman Chemical Company, Kingsport, TN (US)

(*) Notice: Subject to any disclaimer, the term of this patent is extended or adjusted under 35 U.S.C. 154(b) by 0 days.

(21) Appl. No.: 13/755,910

(22) Filed: Jan. 31, 2013

(51) Int. Cl.
   *C07C 29/00* (2006.01)
   *C07C 31/34* (2006.01)

(52) U.S. Cl.
   USPC ............ 568/846; 568/853; 568/854; 568/862

(58) Field of Classification Search
   CPC .......... C07C 31/34; C07C 45/58; C07C 29/38
   USPC .................................. 568/846, 853, 854, 862
   See application file for complete search history.

(56) References Cited

U.S. PATENT DOCUMENTS

| | | | |
|---|---|---|---|
| 3,808,280 A | 4/1974 | Merger et al. | |
| 3,876,706 A | 4/1975 | Levanevsky et al. | |
| 3,886,219 A | 5/1975 | Reich | |
| 3,939,216 A | 2/1976 | Wright | |
| 3,975,450 A | 8/1976 | Palmer et al. | |
| 4,036,888 A | 7/1977 | Couderc et al. | |
| 4,250,337 A | 2/1981 | zur Hausen et al. | |
| 4,386,219 A | 5/1983 | Merger et al. | |
| 4,393,251 A | 7/1983 | Broecker et al. | |
| 4,665,219 A | 5/1987 | Merger et al. | |
| 4,851,592 A | 7/1989 | Morris | |
| 4,855,515 A | 8/1989 | Morris et al. | |
| 4,918,247 A | 4/1990 | Breitkopf et al. | |
| 4,933,473 A | 6/1990 | Ninomiya et al. | |
| 5,072,058 A | 12/1991 | Dambkes et al. | |
| 5,093,537 A | 3/1992 | Unruh et al. | |
| 5,144,088 A | 9/1992 | Salek et al. | |
| 5,146,012 A | 9/1992 | Salek et al. | |
| 5,166,370 A | 11/1992 | Liotta, Jr. et al. | |
| 5,185,478 A | 2/1993 | Salek et al. | |
| 5,334,778 A | 8/1994 | Haas et al. | |
| 5,380,919 A | 1/1995 | Merger et al. | |
| 5,395,989 A | 3/1995 | Yoneoka et al. | |
| 5,532,417 A | 7/1996 | Salek et al. | |
| 5,608,121 A | 3/1997 | Ninomiya et al. | |
| 5,841,002 A | 11/1998 | Harrison et al. | |
| 5,888,923 A | 3/1999 | Chen et al. | |
| 6,018,074 A | 1/2000 | Kratz et al. | |
| 6,077,980 A | 6/2000 | Ninomiya et al. | |
| 6,080,896 A | 6/2000 | Ninomiya et al. | |
| 6,096,931 A | 8/2000 | Frohning et al. | |
| 6,187,971 B1 | 2/2001 | Kratz et al. | |
| 6,201,159 B1 | 3/2001 | Choi et al. | |
| 6,255,541 B1 | 7/2001 | Paatero et al. | |
| 6,268,539 B1 | 7/2001 | Sen-Huang et al. | |
| 6,340,778 B1 | 1/2002 | Bueschken et al. | |
| 6,545,189 B1 | 4/2003 | Nousiainen | |
| 6,552,232 B2 | 4/2003 | Mehnert et al. | |
| 6,586,641 B2 | 7/2003 | Dernbach et al. | |
| 6,593,502 B2 | 7/2003 | Salmi et al. | |
| 6,600,078 B1 | 7/2003 | Mahmud et al. | |
| 6,914,164 B2 | 7/2005 | Koch et al. | |
| 7,060,861 B2 | 6/2006 | Dernbach et al. | |
| 7,087,800 B2 | 8/2006 | Ninomiya et al. | |
| 7,301,058 B2 | 11/2007 | Wartini et al. | |
| 7,368,612 B2 | 5/2008 | Amemiya et al. | |
| 7,388,116 B2 | 6/2008 | Maas et al. | |
| 7,439,406 B2 | 10/2008 | Wartini et al. | |
| 7,462,747 B2 | 12/2008 | Sirch et al. | |
| 7,767,865 B2 | 8/2010 | Sirch et al. | |
| 8,013,192 B2 | 9/2011 | Husen et al. | |
| 2003/0009062 A1 | 1/2003 | Dobert et al. | |
| 2008/0004475 A1 | 1/2008 | Sirch et al. | |
| 2009/0069604 A1 | 3/2009 | Maas et al. | |
| 2010/0113836 A1 | 5/2010 | Sirch et al. | |
| 2011/0098515 A1 | 4/2011 | Schalapski et al. | |
| 2011/0184212 A1 | 7/2011 | Schulz et al. | |
| 2011/0272270 A1 | 11/2011 | Schlitter et al. | |
| 2011/0282106 A1 | 11/2011 | Steiniger et al. | |
| 2011/0313203 A1 | 12/2011 | Sirch et al. | |
| 2011/0313204 A1 | 12/2011 | Zim et al. | |
| 2012/0004472 A1 | 1/2012 | Sirch et al. | |

FOREIGN PATENT DOCUMENTS

| | | |
|---|---|---|
| DE | 10317545 | 4/2004 |
| JP | 4074143 | 3/1992 |
| WO | WO0058246 | 10/2000 |
| WO | WO0058247 | 10/2000 |

OTHER PUBLICATIONS

Synthesis of Neopentyl Glycol, part A; posted Jul. 13, 2010 by China Papers, retrieved on Aug. 31, 2012 from http://mt.china-papers.com/?p=122613, 1 page.

*Primary Examiner* — Sikarl Witherspoon
(74) *Attorney, Agent, or Firm* — Ying Yufan Luo

(57) ABSTRACT

A process for producing polyols (such as neopentyl glycol) is disclosed which comprises reacting formaldehyde and another aldehyde in the presence of a trialkylamine catalyst and a base promoter to form an Aldol condensation reaction product. The base promoter improves removal of nitrogen containing salts prior to hydrogenation of the hydroxy aldehyde to produce the polyol. The improved process also reduces trialkylamine catalyst usage, improves trialkylamine catalyst recovery, and reduces nitrogen-containing salts prior to hydrogenation.

20 Claims, No Drawings

PROCESS FOR PRODUCING POLYOLS

BACKGROUND

Polyols and especially neopentyl glycol (NPG; 2,2-dimethyl-1,3-propanediol) are widely used as starting materials for preparation of various useful products such as lubricants, plastics, surface coatings, surfactants, and synthetic resins. Polyalcohols like NPG are typically produced by a two-step process. The first step is an Aldol condensation of an enolizable aldehyde, such as isobutyraldehyde, with formaldehyde to form a hydroxy aldehyde intermediate such as hydroxypivaldehyde (HPA). The second step is the hydrogenation of the hydroxy aldehyde over a metal containing catalyst to form the polyalcohol such as NPG as shown in Scheme 1.

Scheme 1 Preparation of Polyalcohols by Aldol Condensation and Hydrogenation

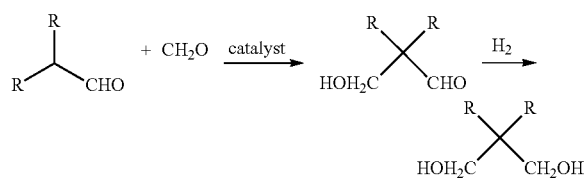

A parameter to watch in the first step of the preparation of polyols is how efficiently the reactants are converted to the hydroxy aldehyde intermediate. The formaldehyde concentration in the Aldol product is frequently considered as an indicator of the efficiency of the reaction because the levels of formaldehyde in the Aldol product can be readily measured by a number of analytical techniques.

Although a large number of catalysts have been previously published, the commercially viable Aldol condensation catalysts can be divided into two groups: (1) a strong alkaline catalyst such as sodium hydroxide or sodium carbonate and (2) a tertiary amine such as TMA or triethylamine.

Alkaline Catalyst Systems

The alkaline catalyst systems have been publically known for many years. In general, these systems are biphasic and consist of a mixture of aldehyde and an aqueous formalin solution. The alkaline catalyst is usually consumed during the process by side reactions such as the Cannizzaro reaction which forms salts of the carboxylic acids that correspond to the aldehydes. Examples of these acids are formic acid, isobutyric acid and hydroxypivalic acid. The salts of the acids need to be removed from the stream prior to distillation and hydrogenation to prevent breakdown to retro Aldol products in the distillation column and hydrogenation reactor. When an excessive amount of formaldehyde is reacted with aldehyde in the presence of a strong alkaline catalyst, large amounts of formate salts are formed as byproducts, making this process commercially unsuitable. On the other hand, when an excessive amount of aldehyde is employed, the excessive amount of aldehyde reacts i) with the product to form esters or ii) with itself to form Aldols and acetals. These byproducts require several additional steps for the purification process and ultimately result in yield loss.

Tertiary Amine Catalyst Systems

The tertiary amine catalyst systems are usually run at a molar ratio with an excessive amount of aldehyde which enables the reaction to be carried out in a homogeneous reaction mixture. In these processes, the selectivity of Aldol is increased compared to the alkaline catalyst systems. The use of tertiary amine catalysts in the Aldol condensation is not perfect.

The tertiary amine catalysts react with organic acids such as formic acid to form salts. Formic acid exists in commercial formaldehyde raw material.

Formaldehyde also reacts with isobutyraldehyde and HPA to form isobutyric acid and hydroxypivalic acid. These acids form salts with the tertiary amine catalyst.

The amine salts cannot be separated from the hydroxy aldehyde by distillation. These amine salts are carried on into the hydrogenation reactor, contacting the metal catalyst therein. The amine salts can deactivate the metal catalyst in the hydrogenation reaction. Further, the amine salts can promote the decomposition of the Aldol condensation product during the distillation of product at high temperatures. Thus, overall yields are dramatically decreased. The amine salts can also cause undesired color and/or odors in the downstream products.

SUMMARY

This invention provides simplified processes of preparing polyols via the Aldol condensation reaction of formaldehyde with another aldehyde to form a hydroxy aldehyde intermediate and hydrogenating the hydroxy aldehyde to form the polyol. Additional details of example methods are further described below in the Detailed Description. This summary is not intended to identify essential features of the claimed subject matter, nor is it intended for use alone in determining the scope of the claimed subject matter.

According to an embodiment, the present invention describes a process for producing a polyol comprising:

contacting formaldehyde and another aldehyde in the presence of an amine catalyst and a promoter under Aldol condensation conditions to produce hydroxy aldehyde; and hydrogenating the hydroxy aldehyde to form a polyol.

Another embodiment describes a process for producing a neopentyl glycol comprising:

contacting formaldehyde and isobutyraldehyde in the presence of an amine catalyst and a promoter under Aldol condensation conditions to produce hydroxypivaldehyde; and hydrogenating the hydroxypivaldehyde to form neopentyl glycol.

Yet another embodiment describes a process for producing a hydroxy aldehyde comprising:

contacting formaldehyde and another aldehyde in the presence of an amine catalyst and a promoter under Aldol condensation conditions to produce hydroxy aldehyde.

DETAILED DESCRIPTION

According to an embodiment, the invention describes a process for reducing the presence of nitrogen containing salts (e.g. amine salts) in a stream of Aldol product prior to the hydrogenation of the stream to polyols. For example, an embodiment concerns reducing nitrogen containing salts from a hydroxy aldehyde, such as HPA, containing stream that is used for the production of a polyol, such as NPG. This invention also describes a method for reusing the amine catalyst in the Aldol condensation reaction in the Aldol reactor.

According to an embodiment, the invention describes a process for the preparation of a polyol. For example, the process comprises i) contacting formaldehyde and another aldehyde in the presence of an amine catalyst and a promoter under Aldol condensation conditions to produce a stream comprising hydroxy aldehyde and nitrogen containing salts and ii) hydrogenating the hydroxy aldehyde to form a polyol.

The hydroxy aldehyde may also optionally be purified before hydrogenation by any means or process that removes low boilers (e.g. unreacted started materials, amine catalyst which has been disassociated from the nitrogen containing salts, and other volatile contaminants that boil-off with water) such as distillation or evaporation. Moreover, the recovered catalyst can be recycled for reuse in the Aldol reactor. For example, the hydroxy aldehyde may be purified by distillation (e.g. on a low boiler removal column), wherein distillation is carried out on the obtained hydroxy aldehyde and nitrogen containing salt stream. The hydroxy aldehyde is freed from water, unreacted starting materials and disassociated catalyst by purification, such as distillation at appropriate combinations of temperature and pressure. Typical conditions may be, for example, a temperature of from about 80° C. to about 135° C.; or from about 85° C. to about 120° C.; or from about 90° C. to about 115° C. Moreover, the distillation pressure can be from about 0 mm to about 1000 mm; or from about 100 mm to about 500 mm; or from about 220 mm to about 300 mm; or even at about 250 mm.

According to an embodiment, examples of another aldehyde include but are not limited to formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalinaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylic aldehyde, capric aldehyde, and glutaraldehyde.

According to an embodiment, examples of the hydroxy aldehyde include but are not limited to 3-hydroxypropanal, dimethylolethanal, trimethylolethanal (pentaerythrital), 3-hydroxybutanal (acetaldol), 3-hydroxy-2-ethylhexanal (butyl aldol), 3-hydroxy-2-methylpentanal (propyl aldol), 2-methylolpropanal, 2,2-dimethylolpropanal, 3-hydroxy-2-methylbutanal, 3-hydroxypentanal, 2-methylolbutanal, 2,2-dimethylolbutanal, and HPA.

According to an embodiment, examples of the polyol include but are not limited to propylene glycol, ethylene glycol, dipropylene glycol, diethylene glycol, 1,4-butanediol, NPG, triethanolamine, and glycerol.

According to an embodiment, the hydroxy aldehyde stream can be prepared by reaction of formaldehyde and another aldehyde in the presence of a tertiary amine catalyst and a promoter. Almost any tertiary amine catalyst may be used. Moreover, examples of such tertiary amines include but are not limited to triethylamine, tri-n-butylamine, and TMA. According to an embodiment, TMA is used due to the low boiling point of TMA compared to reactants and products. The lower boiling point facilitates the distillative or evaporative removal of the nitrogen containing salts in the low boiler removal column once the stronger base promoter has dissociated the amine counter ion.

According to an embodiment, a promoter is supplied to the Aldol reactor which can, among other things, enhance formaldehyde conversion and establish a hydrogenation feed with little to no nitrogen containing salts. The promoter used can be any substance that can achieve dissociation of the nitrogen containing salts due to the strength of the base, measured on a pKa scale, such as inorganic bases. The promoter can include but is not limited to carbonates, hydrogen carbonates, and hydroxides of the alkali metals and the alkaline earth metals. Suitable promoters include but are not limited to $Li_2CO_3$, $Na_2CO_3$, $K_2CO_3$, $CaCO_3$, $LiHCO_3$, $NaHCO_3$, $KHCO_3$, NaOH, LiOH, KOH, and $Ca(OH)_2$. The amount of promoter should be sufficient to remove nitrogen containing salts from the feed to the hydrogenation while not catalyzing the retro Aldol reaction of hydroxy aldehyde to formaldehyde and another aldehyde. The promoter can be used as a solution, such as an aqueous solution, for example, in a concentration of about 5% to about 50% by weight.

The amount of promoter supplied to the Aldol reactor may be determined by the analysis of the hydrogenation feed for nitrogen containing salts which is typically measured as total nitrogen content. The amount of promoter that is added should correspond to the promoter quantity which is sufficient to decompose the amine salts and result in a total nitrogen content in the hydrogenation feed of 25 ppm or less. The amount of promoter will vary because the concentration of the nitrogen containing salts can vary depending on the Aldol reactor variables and raw materials used.

The salts are typically formed from acids in the reaction mixture. These acids are typically formic acid, isobutyric acid, and hydroxypivalic acid. The acids are present in the feedstocks or are formed under reaction conditions. Moreover, the amine catalyst reacts with the acids to form the formate, isobutyrate, and hydroxypivalate salts. Under typical conditions, the concentration of the nitrogen containing salts is from 3000 ppm to 5000 ppm, but as explained above, the concentration can vary based on Aldol reactor variables and raw materials used. It is believed that the promoter breaks up these nitrogen containing salts during the purification (e.g. in the distillation column) to liberate the amine catalyst to be recovered in the low boiler stream. According to an embodiment, about 50 ppm to about 5000 ppm; about 500 ppm to about 3000 ppm; or even about 1000 ppm to about 2000 ppm of promoter is added to the Aldol reactor with the other reactants. Alternatively, the promoter is added to the Aldol reactor at a weight percent excess when compared to the weight percent of the nitrogen containing salts. For example, after the weight percent of the nitrogen containing salts is determined, the promoter can be added to the Aldol reactor at less than a 10 weight percent excess, or less than a 5.0 weight percent excess; or less than a 1.0 weight percent excess when compared to the previously determined weight percent of the nitrogen containing salts.

Scheme 2 below shows an example of a proposed reaction of NaOH (caustic), $Na_2CO_3$ (carbonate), or $NaHCO_3$ (bicarbonate) to deprotonate the ammonium salt. Due to the low boiling nature of TMA, the reaction is driven to completion and the TMA catalyst recovered.

Scheme 2 Reaction of Different Bases with Trimethylammonium Formate Salts

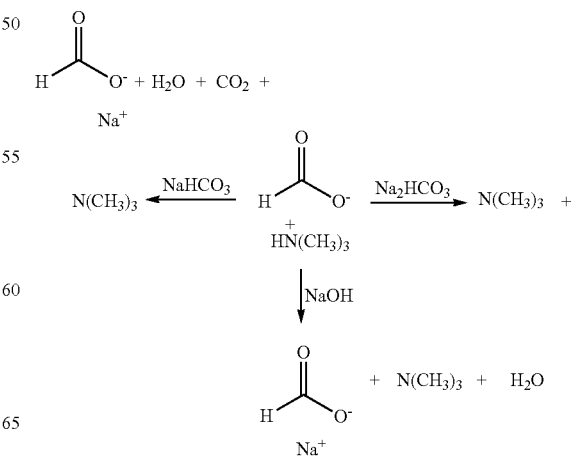

-continued

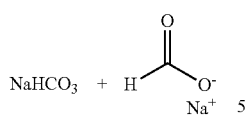

According to an embodiment, the tertiary amine catalyzed reaction is a single phase Aldol reaction. The single phase nature of the reaction occurs because the promoter is in low enough concentration that the process remains a single phase. According to the present process, the combination of the promoter and the amine catalyst results in a highly selective new catalyst that is superior to either the amine or carbonate by themselves for the conversion of formaldehyde.

According to an embodiment, the amount of promoter supplied can be controlled via measurement of the sodium and nitrogen in the hydrogenation feed. In general, the amount of promoter is regulated such that the nitrogen measurement is minimized to a level that is determined by cost benefit analysis. The promoter can be metered in using flow control valves and metering pump. Formaldehyde can be measured at the outlet of the Aldol reactor by any known method. It is typically done with a colorimetric test based on the Hantzsch reaction. The sodium and nitrogen are also measured after purification (e.g. at the outlet of the distillation column) generally by known techniques. Typical sodium analysis can be accomplished with inductively coupled (ICP) optical emissions spectrometer and nitrogen analysis with total nitrogen analyzers (TN-10). All of these measurements can be online or by regular sampling.

According to an embodiment, the hydroxy aldehyde is HPA which can be prepared by reacting isobutyraldehyde and formaldehyde in the presence of a tertiary amine catalyst and promoter. The resulting HPA stream may optionally be purified and then hydrogenated over a metal containing catalyst to form the polyol such as NPG. Suitable metal catalysts include, but are not limited to, metals and compounds of cobalt, nickel, palladium, platinum, rhodium, molybdenum, mixtures thereof, and the like. Other metal catalysts may comprise NiMo, NiCo, CuCr, CoMo, or CoNiMo combinations, in various proportions and mixtures thereof.

The combining or contacting of the formaldehyde and another aldehyde in the presence of the catalyst is carried out under Aldol condensation reaction conditions and the resulting hydroxy aldehyde stream is then hydrogenated over the metal containing catalyst to form the polyol under hydrogenation reaction conditions. The terminology "reaction conditions" is meant to mean those conditions of temperature, pressure, length of contact time, etc., which enable or allow the reaction to proceed. Included in such conditions are those required to supply or to maintain the reactant(s) in the liquid phase, i.e., temperature, pressure, so that intimate contact with the catalyst is realized. Suitable temperatures, for example, may range from about 0° C. to about 200° C.; or from about 20° C. to about 150° C.; or from about 70° C. to about 110° C. Pressures may be varied considerably, and may range from about 1 psig to about 300 psig; from about 5 psig to about 100 psig; or from about 10 psig to about 40 psig. For a batch reaction, total reaction times, i.e., the time to completion or substantial completion of the condensation reaction, will vary considerably, but in general will range from about 30 minutes to about 24 hours or from about 30 minutes to about 2 hours. In the case of a continuous process, with continuous feed to a reaction zone and continuous withdrawal of product containing mixture, average contact time may range from about 30 minutes to about 48 hours or from about 30 minutes to about 2 hours, contact time herein being understood as the liquid volume in the reactor divided by the volumetric flow rate of the liquid.

EXAMPLES

The process according to the embodiments described above is further illustrated by, but not limited to, the following examples wherein all percentages given are by weight unless specified otherwise.

Example 1

Continuous Synthesis of Neopentyl Glycol (NPG)

The process described herein is for the preparation of NPG. A one gallon reactor equipped with a stirrer was continuously fed with isobutyraldehyde, about 50% aqueous formaldehyde solution, and 6% TMA solution in isobutyraldehyde. The ratio of isobutyraldehyde to formaldehyde was maintained in the range of 1.1:1 to 1.6:1 by adjusting the feed rates to the Aldol reactor. Additionally, the TMA concentration in the reactor was adjusted to 2% by adjusting the feed rate of the 6% TMA in isobutyraldehyde solution. The reactor was maintained at 70 to 110° C. under a nitrogen pressure of 10 to 40 psig. The residence time was adjusted to 1 hour by removing the condensation product mixture containing crude HPA at a set rate. This condensation product mixture having the composition shown in Table 1 was introduced continuously to the middle of a multi stage distillation column. The multi staged column was maintained at a sufficient temperature to remove TMA, isobutyraldehyde, and water as overhead products and crude HPA as a base overflow product. Table 1 illustrates the components of the streams when the column bottom temperature was maintained between 80° C. to 100° C. at 5 psig. The overhead product was returned to the Aldol reactor as the TMA catalyst feed.

The base overflow stream was fed continuously to a trickle bed hydrogenation reactor containing a nickel catalyst. The hydrogenation reactor was maintained at 140° C. to 180° C. and 400 to 600 psig of hydrogen pressure. The ratio of total liquid feed volume to fresh feed was maintained at 10:1. The gas and liquid leaving the hydrogenation reactor pass through a vapor liquid separator and the excess hydrogen is vented.

The liquid hydrogenation product stream having the composition shown in Table 1 was treated with sodium hydroxide at 90° C. and then distilled to remove isobutanol, methanol, and water at 100° C. and 760 mm Hg. The NPG/water mixture was flash distilled from sodium containing salts at 150° C. and 130 mm Hg. A final distillation to remove water produces NPG final product in a 95% yield from isobutyraldehyde and with the composition shown in Table 1.

TABLE 1

|  | Aldol (wt %) | Hydrogenation Feed (wt %) | Hydrogenation Product (wt %) | Final Product (wt %) |
|---|---|---|---|---|
| Water | 25 | 20 | 20 | 0 |
| iBOH | 7.5 | — | — | 0 |
| TMA and salts | 1.95 | 0 | — | 0 |
| HPA | 61.5 | 75 | 0.0 | 0 |
| NPG | 0.75 | 0.87 | 75 | 99.8 |
| HCHO (ppm) | 3000 | 250 | 0 | 0 |

TABLE 1-continued

| | Aldol (wt %) | Hydrogenation Feed (wt %) | Hydrogenation Product (wt %) | Final Product (wt %) |
|---|---|---|---|---|
| Nitrogen (ppm) | NM | 1050 | NM | 0 |
| Sodium (ppm) | NM | 0 | NM | 0 |
| Others | 3 | 4 | 5 | 0.2 |

24 hr averages; NM = Not Measured

Example 2

Addition of Sodium Carbonate to the Aldol Reactor

The procedure of Example 1 was repeated except that an additional feed line was added to the existing Aldol reactor feed header. A 6% solution of sodium carbonate was continuously metered into the reactor to maintain 1000 to 1500 ppm sodium in the hydrogenation feed analysis. The resulting total nitrogen measurement in the hydrogenation feed stream was controlled to less than 25 ppm. Additionally, the formaldehyde concentration in the Aldol product (exiting the reactor) was decreased from about 3000 ppm to 1250 ppm. This data demonstrate that the addition of sodium carbonate to the Aldol reactor with TMA results in both TMA recovery prior to hydrogenation reactor and enhanced catalytic properties for the production of HPA.

Example 3

Addition of Sodium Bicarbonate to the Aldol Reactor

The procedure of Example 1 was repeated except that an additional feed line was added to the existing Aldol reactor feed header. A 6% solution of sodium bicarbonate was continuously metered into the reactor to maintain 1000 to 1500 ppm sodium in the hydrogenation feed analysis. The resulting total nitrogen content in the hydrogenation feed stream was controlled to less than about 25 ppm. However, the formaldehyde concentration in the Aldol product (exiting the reactor) did not change from about 3000 ppm. This shows that the basicity of the bicarbonate is sufficient to break up the TMA salts but it is not strong enough to impact the formaldehyde conversion in the Aldol reactor.

Example 4

Addition of Sodium Carbonate to the HCHO Feed

The procedure of Example 1 was repeated except a 6% solution of sodium carbonate was metered into the formaldehyde feed line prior to the Aldol reactor as such a rate as to maintain 1000 to 1500 ppm sodium in the hydrogenation feed analysis. The resulting total nitrogen in the hydrogenation feed was controlled to less than 25 ppm and the formaldehyde concentration in the Aldol product exiting the reactor was decreased from about 3000 ppm to 1250 ppm. This data demonstrates that the addition of sodium carbonate to the formaldehyde feed has the same effect as adding it directly to the Aldol reactor.

Example 5

Decrease Trimethylamine Concentration in the Aldol Reactor

The procedure of example 2 was repeated. A solution of 6% aqueous sodium carbonate was metered into the Aldol reactor to maintain 1000 to 1500 ppm sodium in the hydrogenation feed analysis. The TMA level in the reactor was reduced from 2% to 1%. The resulting total nitrogen in the hydrogenation feed was controlled to less than 25 ppm and the formaldehyde concentration in the Aldol product exiting the reactor was 1250 ppm. This data shows that the addition of sodium carbonate to the Aldol reactor promotes the Aldol reaction sufficiently that the TMA content in the reactor can be substantially reduced and achieve the same conversion of formaldehyde.

Although embodiments have been described in language specific to methodological acts, the embodiments are not necessarily limited to the specific acts described. Rather, the specific acts are disclosed as illustrative forms of implementing the embodiments.

What is claimed is:

1. A process for producing a polyol comprising:
   contacting formaldehyde and another aldehyde in the presence of an amine catalyst and a promoter under Aldol condensation conditions to produce hydroxy aldehyde; and
   hydrogenating the hydroxy aldehyde to form a polyol.

2. The process according to claim 1, further comprising purifying said hydroxy aldehyde prior to hydrogenation and recovering said amine catalyst.

3. The process according to claim 1, wherein the polyol is propylene glycol, ethylene glycol, dipropylene glycol, diethylene glycol, 1,4-butanediol, neopentyl glycol, triethanolamine, or glycerol.

4. The process according to claim 1, wherein the hydroxy aldehyde is 3-hydroxypropanal, dimethylolethanal, trimethylolethanal (pentaerythrital), 3-hydroxybutanal (acetaldol), 3-hydroxy-2-ethylhexanal (butyl aldol), 3-hydroxy-2-methylpentanal (propyl aldol), 2-methylolpropanal, 2,2-dimethylolpropanal, 3-hydroxy-2-methylbutanal, 3-hydroxypentanal, 2-methylolbutanal, 2,2-dimethylolbutanal, or hydroxypivaldehyde.

5. The process according to claim 1, wherein said another aldehyde is formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalinaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylic aldehyde, capric aldehyde, or glutaraldehyde.

6. The process according to claim 1, wherein the amine catalyst is triethylamine, tri-n-propylamine, tri-n-butylamine, trimethlyamine, or mixtures thereof.

7. The process according to claim 1, wherein the promoter is an alkali metal or alkaline earth metal of a carbonate, a hydrogen carbonate, a hydroxide, or mixtures thereof.

8. The process according to claim 7, wherein the promoter is $Na_2CO_3$, $K_2CO_3$, $CaCO_3$, $NaHCO_3$, $KHCO_3$, NaOH, KOH, $Ca(OH)_2$, or combinations thereof.

9. A process for producing neopentyl glycol comprising:
   contacting formaldehyde and isobutyraldehyde in the presence of an amine catalyst and a promoter under Aldol condensation conditions to produce hydroxypivaldehyde; and
   hydrogenating the hydroxypivaldehyde to form neopentyl glycol.

10. The process according to claim 9, further comprising purifying said hydroxypivaldehyde prior to hydrogenation and recovering said catalyst.

11. The process according to claim 9, wherein the amine catalyst is triethylamine, tri-n-propylamine, tri-n-butylamine, trimethlyamine, or mixtures thereof.

12. The process according to claim 9, wherein the promoter is an alkali metal or alkaline earth metal of a carbonate, a hydrogen carbonate, a hydroxide, or mixtures thereof.

13. The process according to claim 12, wherein the promoter is $Na_2CO_3$, $K_2CO_3$, $CaCO_3$, $NaHCO_3$, $KHCO_3$, NaOH, KOH, $Ca(OH)_2$, or combinations thereof.

14. A process for producing a hydroxy aldehyde comprising:
    contacting formaldehyde and another aldehyde in the presence of an amine catalyst and a promoter under Aldol condensation conditions to produce hydroxy aldehyde.

15. The process according to claim 14, further comprising purifying said hydroxy aldehyde and recovering said catalyst.

16. The process according to claim 14, wherein the hydroxy aldehyde is 3-hydroxypropanal, dimethylolethanal, trimethylolethanal (pentaerythrital), 3-hydroxybutanal (acetaldol), 3-hydroxy-2-ethylhexanal (butyl aldol), 3-hydroxy-2-methylpentanal (propyl aldol), 2-methylolpropanal, 2,2-dimethylolpropanal, 3-hydroxy-2-methylbutanal, 3-hydroxypentanal, 2-methylolbutanal, 2,2-dimethylolbutanal, or hydroxypivaldehyde.

17. The process according to claim 14, wherein said another aldehyde is formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalinaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylic aldehyde, capric aldehyde, or glutaraldehyde.

18. The process according to claim 14, wherein the amine catalyst is triethylamine, tri-n-propylamine, tri-n-butylamine, trimethlyamine, or mixtures thereof.

19. The process according to claim 14, wherein the promoter is an alkali metal or alkaline earth metal of a carbonate, a hydrogen carbonate, a hydroxide, or mixtures thereof.

20. The process according to claim 19, wherein the promoter is $Na_2CO_3$, $K_2CO_3$, $CaCO_3$, $NaHCO_3$, $KHCO_3$, NaOH, KOH, $Ca(OH)_2$, or combinations thereof.

* * * * *